United States Patent [19]
Mazzetti

[11] 4,056,983
[45] Nov. 8, 1977

[54] FLOW DIVERSION SAMPLER

[76] Inventor: Flavio J. Mazzetti, 6580 Arequa Ridge Lane, Colorado Springs, Colo. 80919

[21] Appl. No.: 720,135

[22] Filed: Sept. 3, 1976

[51] Int. Cl.$^2$ ............................................. G01N 1/20
[52] U.S. Cl. .................................................. 73/423 R
[58] Field of Search ......................... 73/422 R, 423 R

[56] References Cited

U.S. PATENT DOCUMENTS

| | | | |
|---|---|---|---|
| 3,279,260 | 10/1966 | Huntington | 73/423 R |
| 3,561,273 | 2/1971 | Tanila | 73/423 R |
| 3,986,402 | 10/1976 | Irwin | 73/423 R |

*Primary Examiner*—S. Clement Swisher
*Attorney, Agent, or Firm*—Richard W. Hanes

[57] ABSTRACT

A sampling device for taking a complete cross section of a stream of material flowing through a conduit system. The device consists of a container into which material is fed through a flexible conduit that can be moved to discharge either into a main conduit or into a sampling conduit within the container. The flexible conduit is moved by a reciprocating rod pivotally attached to a collar on the end of the flexible conduit. A timing device controls the operation of a motor which drives the rod. A sealing member is also pivotally attached to the collar and rod and is positioned over the sampling conduit between samplings to prevent entry of any contaminating material. The seal cooperates with blades on the entrance to the sampling conduit to form a tight seal. The pivoting of the seal member is limited to a predetermined arc by contact with the collar. This limiting feature serves to insure a tight seal while allowing the seal to adjust for minor wear and misalignment. The flexible conduit sweeps the flow across the entrance of the sampling conduit at a right angle. A blade on the bottom wall of the sampler minimizes any disturbance of the flow as it is moved up into alignment with the sampler by neatly cutting into the oncoming flow. The sampling conduit has an adjustable top wall which controls the size of the entrance. This wall can be adjusted before, during, or at any point in the operation.

1 Claim, 7 Drawing Figures

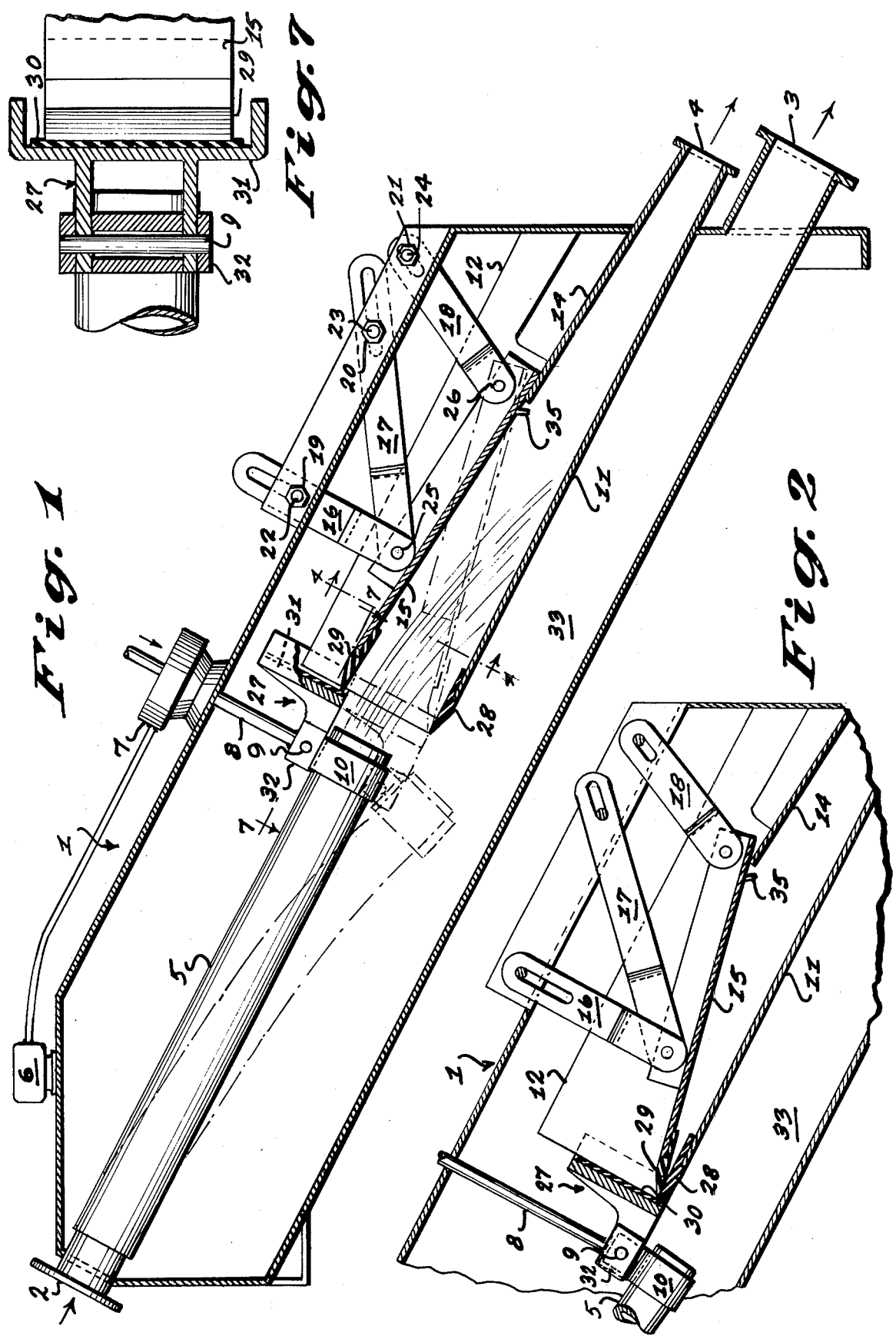

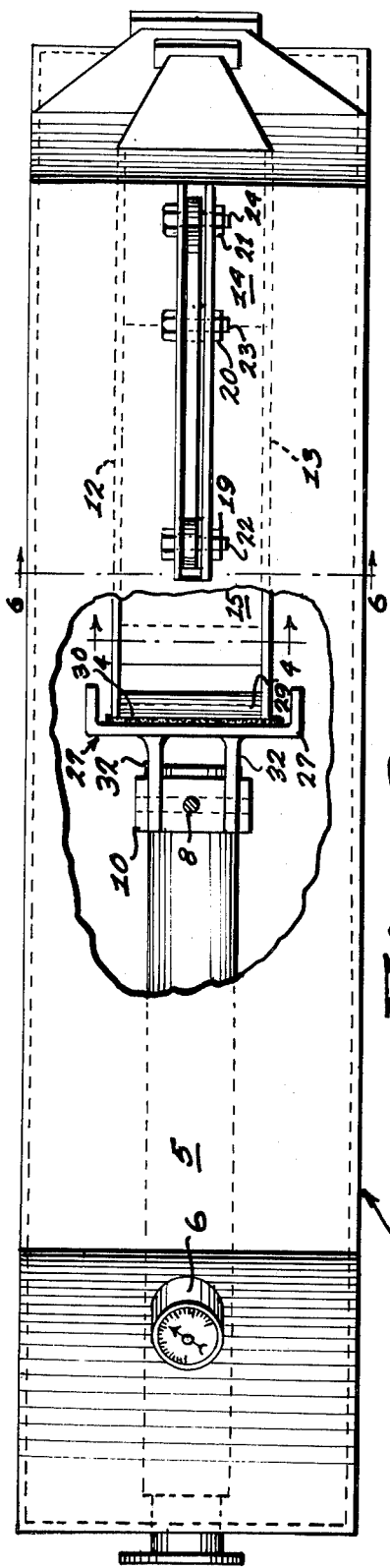
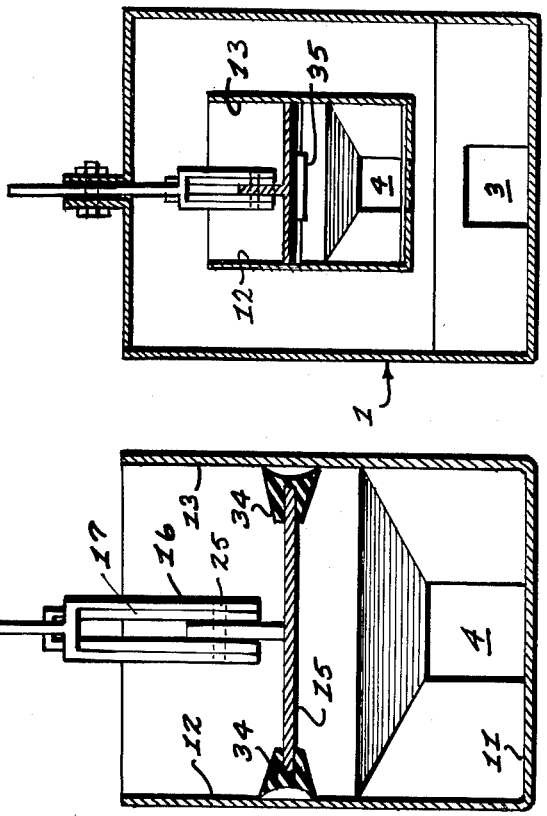
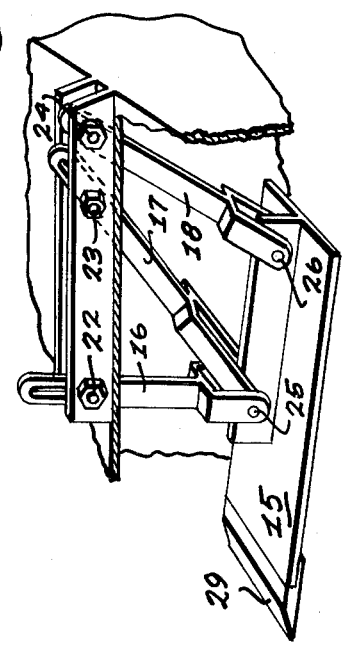

FLOW DIVERSION SAMPLER

BACKGROUND OF THE INVENTION

Sampling is an essential part of quality control and business economics. To get a truly representative sample of a moving stream of material, it is essential to capture a complete cross section and to seal the sampler from any contaminating fluid, dust, or material between samplings.

PRIOR ART

A known way to sample a material flowing through a conduit system is to provide a movable conduit segment along the flow path. When a sample is desired, the movable segment is shifted so that the flow is diverted to a sample receiving chamber. After a sample is taken, the segment is moved back so that the flow is again going into the main receiver. Prior art of this general type includes U.S. Pat. No. 2,518,574 to Skopecek, U.S. Pat. No. 3,555,911 to Cordell et al, and U.S. Pat. No. 2,625,952 to Eide et al. None of these, however, attempts to seal the sampler from any contaminating fluid, dust, or material between samplings.

U.S. Pat. No. 3,750,478 to Keene shows the use of a sealing member in a sampler. Keene employs a diverter to switch most of the flow from one conduit to another. As the diverter is rotated to its diverting position, it pushes open a pivotable seal that normally covers the entrance to the second conduit. Applicant's invention accomplishes this same desired sealing in a different environment and in an improved fashion as described below.

BRIEF SUMMARY OF THE INVENTION

It is an object of this invention to provide a sampler that captures an entire cross section of a moving stream of material all at one time.

It is a further object of this invention to provide a sampler that is sealed from any contaminating fluid, dust, or material between samplings.

It is also an object to provide a sampler that minimizes disturbance of the flow during the sampling process. To accomplish this, the invention sweeps the main flow across the entrance to the sampler at a 90° angle and provides a sharp blade at the inlet to the sampler which neatly cuts the flow as it is being moved up into alignment with the sampler.

It is also an object to provide a sample that is particularly useful for sampling fluids containing solid particles.

BRIEF DESCRIPTION OF THE DRAWINGS

FIG. 1 is a side view of the sampler container and sampling conduit with portions broken away and shown in cross section and showing the sampler in operation with the full flow of material being received into the sampling conduit. The phantom lines show the movable delivery conduit emptying into the main receiver and the inlet of the sampling conduit being sealed during this time.

FIG. 2 is a side view of the linkage system that provides adjustment of the size of the entrance to the sampling conduit.

FIG. 3 is a top plan view of the invention with a portion of the top of the container broken away to reveal a portion of the sampler conduit.

FIG. 4 is a cross sectional view of the sampling conduit taken along lines 4—4 of FIGS. 1 and 3 showing the sealing arrangement between the adjustable top wall of the sampling conduit and the side walls of the conduit.

FIG. 5 is a prospective view of the linkage system that controls the positioning of the top wall of the sampling conduit.

FIG. 6 is a cross sectional view of the sampler container taken along lines 6—6 of FIG. 3.

FIG. 7 is a view taken along 7—7 of FIG. 1 showing the relationship between the adjustable top wall of the sampler conduit and the sealing cover.

DETAILED DESCRIPTION OF THE INVENTION

As best seen in FIG. 1, container 1 has one inlet 2 and two outlets 3 and 4. Outlet 3 is the main one through which the flow normally passes. Outlet 4 is the one through which the sample passes. Material enters through inlet 2 and passes through flexible conduit 5. Depending upon the location of the outlet of flexible conduit 5, the material will ultimately leave the container 1 through either outlet 3 or 4. Timer 6 activates drive means 7 which controls the movement of rod member 8. The drive means can be any reciprocating type, such as a solenoid, hydraulic or pneumatic cylinder, or a reducer-brake type motor, that will confine the longitudinal movement of rod 8 to roughly along the same axis. Rod 8 is pivotally attached by pin 9 to a collar 10 on the outlet end of the flexible conduit 5.

The preferred conduit means for receiving the sample from flexible conduit 5 is shown in the drawing as having flat walls (see FIGS. 1, 3, 4 and 6). Other shapes are equally applicable to Applicant's invention. As shown in FIG. 1, stationary plate 11 forms the bottom wall of the sampling conduit and stationary plates 12 and 13 as seen in FIGS. 4 and 6 form the side walls. Referring back to FIG. 1, the top wall of the sampling conduit has two parts, a stationary plate 14 and an adjustable one 15. As seen in FIGS. 1, 2, and 5, the position of the adjustable plate 15 is controlled by links 16, 17 and 18. Any desired opening size for the sampling conduit can be set by loosening nuts 19, 20 and 21, adjusting the plate 15 and links to the desired position, and retightening the nuts. The links are rotatably attached to the container 1 by bolts 22, 23 and 24 and to the plate 15 by pins 25 and 26. Link 18 is always set so that the back of plate 15 fits tightly against plate 14. Rib 35 on the lower side of the cover plate 15 serves to prevent leakage by diverting flow away from the joint between plates 14 and 15.

As seen in FIG. 1, the cover 27 and blades 28 and 29 on the ends of plates 11 and 15 serve to form a sealing arrangement over the inlet to the sampling conduit when the conduit 5 is in its lowered position. This sealing arrangement functions to seal the inlet from any contaminating material between samplings, an essential feature in taking an accurate sample. In the preferred embodiment of FIGS. 1 and 3, the cover 27 comprises a pair of brackets carrying a seal plate 31 conforming generally to the shape of the inlet to the sampler and having a U-shaped cross section with straight, perpendicular sides which act as splash guards when the cover is in closing position over the inlet. In the closed position, an elastomer facing member 30 attached to the inside of the seal plate 31 forms a sealing arrangement with the blades 28 and 29.

As seen in FIGS. 1-3, the cover 27 has a bracket projection 32 and is pivotally connected to the collar 10 and rod 8 by pin 9. This pivotal freedom helps the seal to adjust for minor operating misalignments or wear. The pivotal rotation of the seal about pin 9 is limited to a predetermined arc by contact between a portion of projection 32 of the cover and the collar 10. This helps to make the sealing arrangement of the cover 27 with blades 28 and 29 as tight as possible.

FIG. 4 shows the seals 34 which are attached to the sides of plate 15.

In normal operation, timer 6 has operated drive means 7 to lower rod 8 so that flexible conduit 5 is discharging flow into the main receiver 33 of container 1 and cover 27 is firmly over the inlet to the sampling conduit. Before, during, or at any point in the operation, adjustable top plate 15 of the sampling conduit can be set to the desired height so that the entire cross section of the flow enters the conduit. Correct setting of the height helps to reduce turbulance during the sampling.

When a sample is to be taken, timer 6 activates driving means 7 which lifts rod 8. By means of the pivotal attachment of the rod to the collar 10 of the flexible conduit 5 and to the seal 27, the seal is raised above the inlet to the sampling conduit as the flexible conduit is lifted into alignment with the inlet. During the lift, the flow is swept by the lower blade 28 at roughly 90° by the rising conduit 5. The blade serves to minimize any disturbance of the flow pattern during the sweep by making a neat cut in the flow as it passes.

Once a complete cross sectional sample is received, conduit 5 and cover 27 are then lowered into their normal operating positions with conduit 5 emptying into the main receiver 33 of container 1 and cover 27 positioned firmly over the inlet to the sampling conduit.

I claim:

1. A sampling device for diverting a confined stream of fluid material from a first to a second course, comprising:
    a housing disposed in series with the stream flow and having a single inlet defined by an inwardly projecting flexible conduit for directing the stream flow interiorly of the housing, said flexible conduit having a discharge mouth;
    and wherein said housing includes first and second discharge ports, said second discharge port defined by a duct projecting interiorly of the housing;
    drive means attached to the said flexible conduit and disposed to move the said discharge mouth into alignment with the said duct, wherein said duct includes at least one movable wall whereby the size of the duct inlet may be altered;
    and including cover means operably connected to the drive means, disposed and positioned to cover the duct inlet when the flexible conduit discharge mouth and the duct inlet are misaligned.

* * * * *